United States Patent [19]

Petinaux et al.

[11] 4,176,118
[45] Nov. 27, 1979

[54] AROMATIC URETDIONE-DIISOCYANATE-DISULPHONIC ACIDS

[75] Inventors: Marcel Petinaux, Krefeld; Dieter Dieterich, Leverkusen; Peter Markusch, Cologne, all of Fed. Rep. of Germany

[73] Assignee: Bayer Aktiengesellschaft, Leverkusen, Fed. Rep. of Germany

[21] Appl. No.: 848,969

[22] Filed: Nov. 7, 1977

Related U.S. Application Data

[63] Continuation of Ser. No. 690,494, May 27, 1976, abandoned.

[30] Foreign Application Priority Data

Jun. 3, 1975 [DE] Fed. Rep. of Germany ....... 2524476

[51] Int. Cl.² .......................................... C07D 205/10
[52] U.S. Cl. ................................................ 260/239 A
[58] Field of Search .................................... 260/239 A

[56] References Cited

U.S. PATENT DOCUMENTS 3,595,329   5/1976   Dieterich et al. ............ 260/453 AR

FOREIGN PATENT DOCUMENTS 2359614   5/1975   Fed. Rep. of Germany .

OTHER PUBLICATIONS

Bordwell et al., J. Amer. Chem. Soc. 81, 1999-2002.
Terent'ev et al., Chem. Abs. 55, 18659f (1960).

*Primary Examiner*—Mark L. Berch
*Attorney, Agent, or Firm*—Gene Harsh; Joseph C. Gil; R. Brent Olson

[57] ABSTRACT

This invention relates to new aromatic uretdione-diisocyanate-disulphonic acids, to a process for the preparation thereof and to the use thereof as components for the production of polyurethane resins. More particularly, the instant invention relates new aromatic uretdione-diisocyanate-disulphonic acids of the general formula:

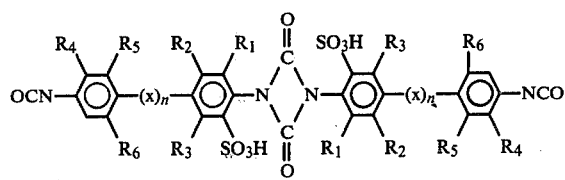

wherein $R_1$, $R_2$, $R_3$, $R_4$, $R_5$ and $R_6$ each represent a hydrogen, chlorine or bromine atom or a methyl, ethyl or $C_1$-$C_4$ alkoxy group;

x represents —O—, >C=O, >SO₂,

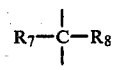

or —CH=CH— wherein $R_7$ and $R_8$ each represent a hydrogen atom, a methyl or ethyl group or, when taken together with the carbon atom to which they are attached represent a cyclohexyl group; and n represents 0 or 1.

These novel compounds are prepared by reacting a diisocyanate of general formula:

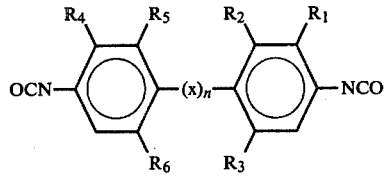

wherein $R_1$, $R_2$, $R_3$, $R_4$, $R_5$, $R_6$, n and x are as defined above with $SO_3$ at temperatures of from −30° to +100° C. in anhydrous solvents which are inert towards $SO_3$ and isocyanate groups.

9 Claims, No Drawings

AROMATIC URETDIONE-DIISOCYANATE-DISULPHONIC ACIDS

This is a continuation of application Ser. No. 690,494 filed May 27, 1976, now abandoned.

BACKGROUND OF THE INVENTION

Aromatic diisocyanates which contain sulphonic acid groups are known (German Offenlegungsschrift No. 1,939,911). The reaction of tolylene diisocyanate with sulphur trioxide, for example, results in a crystalline, high melting product which dissolves by a rapid reaction in sodium hydroxide solution. The resultant product may be used, for example, for the preparation of anionic polyurethane dispersions. From German Offenlegungsschrift No. 2,227,111 which corresponds to U.S. continuation-in-part application Ser. No. 528,319 filed on Dec. 17, 1974 it is also known that polyisocyanates which contain sulphonic acid and/or sulphonate groups, and in which uretdione derivatives are present in addition to other reaction products, may be obtained by the sulphonation of liquid multicomponent mixtures of aromatic polyisocyanates (see also German Offenlegungsschrift No. 2,359,614 which corresponds to U.S. patent application Ser. No. 527,473 filed on Nov. 26, 1974).

DESCRIPTION OF THE INVENTION

It has now been found that novel aromatic tetranuclear uretdione diisocyanate disulphonic acids corresponding to the following formula:

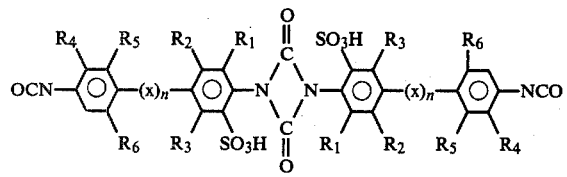

wherein
$R_1$, $R_2$, $R_3$, $R_4$, $R_5$ and $R_6$ each represent a hydrogen, chloride or bromine atom or a methyl, ethyl, or $C_1$–$C_4$ alkoxy group;
x represents —O—, >C=O, >SO$_2$,

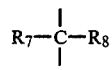

or —CH=CH—
wherein $R_7$ and $R_8$ each represent a hydrogen atom or a methyl of ethyl group or, together with the carbon atom to which they are attached, represent a cyclohexyl group; and
n represents 0 or 1;
are obtained as crystalline powders when solid diisocyanates corresponding to the following formula:

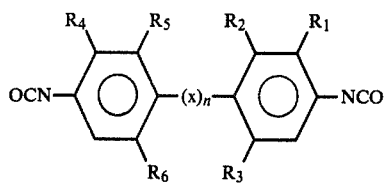

wherein $R_1$, $R_2$, $R_3$, $R_4$, $R_5$, $R_6$, n and x are as defined above; are sulphonated at temperatures of from −30° to +100° C. with sulphur trioxide in anhydrous solvents which are inert towards SO$_3$ and isocyanate groups.

The present invention thus relates to the above-mentioned new uretdione diisocyanate disulphonic acids.

The present invention also relates to a process for the preparation of these new compounds, which is characterized in that a diisocyanate corresponding to the following general formula:

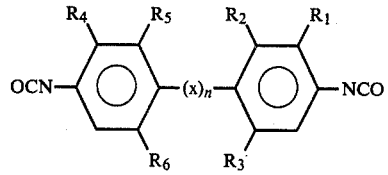

wherein $R_1$, $R_2$, $R_3$, $R_4$, $R_5$, $R_6$, n are x are as defined above; is reacted with sulphur trioxide at temperatures of from −30° to +100° C. in anhydrous solvents which are inert towards SO$_3$ and isocyanate groups.

Finally, the present invention relates to the use of the above-mentioned novel uretdione diisocyanate disulphonic acids as reactants which are to be reacted with compounds containing groups which are reactive with isocyanate groups for the production of polyurethane resins by the known isocyanate polyaddition process.

It is highly surprising that in the process of the present invention the formation of uretdione proceeds quantitatively in an acid medium under sulphonation conditions since according to the literature (High Polymers, volume XVI, "Polyurethanes, Chemistry and Technology", by Saunders-Frisch, Interscience Publishers, New York, London, Volumn I, 1962, page 91), the isocyanate dimerisation reactions previously known take place under basic reaction conditions or with specific phosphine catalysts. Another remarkable finding is that, starting from diisocyanates, clearly defined diisocyanate disulphonic acids containing a uretdione ring are formed and not higher molecular weight polyuretdiones, such as are formed from the corresponding diisocyanates under phosphine catalysis. According to NMR spectroscopic investigations (see Examples), the sulphonic acid groups in the compounds of the present invention are without exception in the ortho-position to the isocyanate groups which form the uretdione groups in the products. Consequently, only two of the four aromatic nuclei present are selectively sulphonated. The whole process is surprising since selective sulphonation at one of the two aromatic nuclei and selective dimerisation of the adjacent isocyanate group take place simultaneously in one reaction step.

It was known from German Offenlegungsschrift No. 2,227,111 that the partial sulphonation of liquid aromatic polyisocyanates, resulting in the formation of liquid polyisocyanates which contain sulphonic acid groups, but whose structure is not specifically defined, may also be accompanied by the formation of uretdione groups which are detectable in the IR spectrum. However, it could not be deduced from this finding that the stoichiometric sulphonation of a dinuclear aromatic 4,4'-diisocyanate would result in the formation of a specific uretdione sulphonic acid.

It is striking that, even when sulphonation is carried out on 4,4'-diisocyanatodiphenylmethane, a compound which, as is well known, contains two isocyanate groups of equal and pronounced reactivity, the reaction product is found to consist almost exclusively of the mono-uretdione disulphonic acid. Dimerisation of a sulphonated diisocyanate with an unsulphonated diisocyanate which would thermodynamically be possible, does not occur. The second aromatic nucleus carrying an isocyanate group is neither sulphonated nor dimerised.

The sulphonation reaction may be carried out under anhydrous conditions with $SO_3$ or with organic compounds in which $SO_3$ is bound by addition. The $SO_3$ may be used in liquid form or in gaseous form, for example diluted with nitrogen.

Suitable organic compounds containing $SO_3$ bound by addition are, in particular, pyridine-$SO_3$, dioxane-$SO_3$, tetrahydrofuran-$SO_3$, ether-$SO_3$ and dimethylformamide-$SO_3$, but it is preferable to carry out the sulphonation with gaseous $SO_3$ diluted in a stream of nitrogen.

The other starting compounds for the process according to the present invention are isocyanates corresponding to the following general formula:

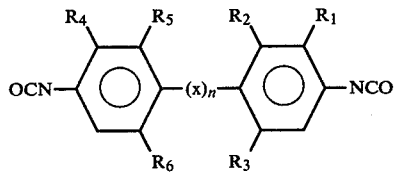

wherein $R_1$, $R_2$, $R_3$, $R_4$, $R_5$, $R_6$, n and x are as defined above.

These starting compounds are preferably diisocyanates corresponding to the above formula wherein $R_1$ and $R_4$ represent hydrogen or a methyl group, $R_2$, $R_3$, $R_5$ and $R_6$ represent hydrogen, x represents a methylene bridge and n represents 1.

The following are examples of such diisocyanates: 4,4'-diisocyanatodiphenylmethane, 3,3'- and 2,2'-dimethyl-4,4'-diisocyanatodiphenylmethane, 2,5,2',5'-tetramethyl-4,4'-diisocyanatodiphenylmethane, 3,3'-dimethoxy-4,4'-diisocyanatodiphenylmethane, 3,3'-dichloro-4,4'-diisocyanatodiphenylmethane, 4,4'-diisocyanato-dimethylmethane, 4,4'-diisocyanato-diphenylcyclohexylmethane, 4,4'-diisocyanato-benzophenone, 4,4'-diisocyanato-diphenylsulphone, 4,4'-diisocyanatodiphenylether, 4,4'-diisocyanato-3,3'-dibromodiphenylmethane, 4,4'-diisocyanato-3,3'-diethyl-diphenyl-methane , and 4,4'-diisocyanatodiphenylethylene-(1,2).

The solvents used must be chemically inert both towards $SO_3$ and towards the diisocyanates under the reaction conditions. The preferred solvents are halogenated or nitrated hydrocarbons, such as dichloroethane, tetrachloroethane, methylene chloride, chloroform, fluorotrichloromethane, nitromethane, and nitrobenzene; ethers, such as dioxane, tetrahydrofuran, and pyridine; and sulphur dioxide.

The reaction is preferably carried out using a molar ratio of diisocyanate: $SO_3$ of from about 1:1 to about 1:1.4 although a greater excess of $SO_3$ may be used without substantially altering the course of the reaction. $SO_3$ may also be used in a subequivalent amount and the unreacted diisocyanate may then be recovered, or recycled if the process is carried out continuously.

The process is carried out at temperatures of from $-30°$ to $+100°$ C., preferably from $-10°$ to $+30°$ C. and most preferably from $-5°$ to $+10°$ C. The diisocyanate is preferably introduced into the reaction vessel as a solution in anhydrous solvent, and $SO_3$ evaporated in a stream of nitrogen is passed over the surface of the mixture while the mixture is vigorously stirred and the temperature is preferably maintained within the above-mentioned preferred range by cooling. The uretdiones of the present invention are obtained as white or pink solids and preferably pulverulent crystalline products which are insoluble in organic solvents. They generally do not have a melting point and in dilute alkaline hydroxide solution they dissolve immediately with decomposition. Sulphonation may also be achieved by combining a solution of the diisocyanate used as starting material with a solution of $SO_3$ or of its adducts.

The mother liquors left after the reaction may be used again for subsequent batches.

As was to be expected, the new substances react as diisocyanates at elevated temperatures in accordance with the known diisocyanate polyaddition process, for example with glycols, polyamines or high molecular weight polyols, such as polyethers or polyesters, to form the corresponding polyurethanes, polyureas, or polyurethane polyureas. Due to the presence of one sulphonic acid group per mol of diisocyanate put into the process, the isocyanatouretdiones are virtually non-toxic products which again give rise to non-toxic substances (aminosulphonic acids) when the polymers produced from them undergo decomposition. Furthermore, the products have no measurable vapor pressure. The isocyanatouretdiones of the present invention therefore have many and varied possible used as physiologically harmless diisocyanates, for example as components for the synthesis of products by the diisocyanatopolyaddition process, as cross-linking agents, and for the production of polyisocyanurates, polycarbodiimides, polyimides or polyhydantoins. Owing to their highly polar or ionic character, these uretdione diisocyanates are particularly suitable for the synthesis of water-soluble or water-dispersible polyurethanes and polyurethane ureas.

Both the uretdione diisocyanates as such and the reaction products thereof are suitable, for example, for the preparation of binders and impregnating agents, in particular for inorganic or mineral substrates. They are also suitable for the synthesis of ionomers which are cross-linked by physical means, as well as cation exchangers and membranes. These uretdione diisocyanates may also be mixed with compounds which contain hydroxyl groups to produce plastisols which are stable in storage and harden at temperatures above 100° C.

EXAMPLE 1

500 g (2 mol) of 4,4'-diisocyanato-diphenylmethane are dissolved in 1000 ml of 1,2-dichloroethane. The solution is vigorously stirred while a stream of $SO_3$/nitrogen (0.5 mol of $SO_3$ per hour) obtained by evaporating 101 ml (2.4 mol) of freshly distilled $SO_3$ in a stream of nitrogen at 130° C. is passed over the surface of the solution at from $-5°$ to $+5°$ C. The quantity of nitrogen used is adjusted so that no SO₃ leaves the reaction vessel. Stirring is then continued until the reaction mixture has warmed to room temperature, and the mixture is then suction filtered. 470 g (yield 71% of the theoretical yield) of the uretdione of the following formula:

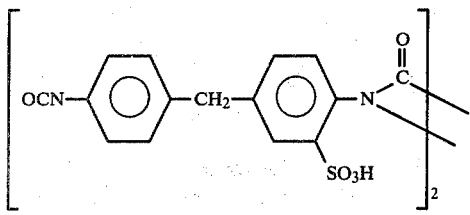

is obtained as a pink powder. M.p. > 280° C. with decomposition.

| Analysis: | C % | H % | N % | O % | S % |
|---|---|---|---|---|---|
| Calculated: | 54.5 | 3.0 | 8.5 | 24.3 | 9.7 |
| Observed: | 53.8 | 3.4 | 8.6 | 23.9 | 10.1 |

IR spectrum: 2275 cm⁻¹ (intense) NCO band; 1790 cm⁻¹ (intense and broad) uretdione band; 1180 cm⁻¹ (broad) SO₃H band.

The appearance of the IR bank at 1790 cm⁻¹ proves the presence of an SO₃H group in the ortho-position to the uretdione group since the uretdione band is normally situated at about 1765 cm⁻¹ when uretdiones are unsubstituted in the ortho-position. The constitution indicated was, incidentally, also confirmed by NMR spectroscopic investigations. When the reaction product is treated with deuterated dilute alkali liquor, it dissolves with evolution of CO₂ and the sulphanilic acid derivative formed under these conditions gives signals at between 6.75 and 7.50 ppm which represent a characteristic aromatic proton resonance spectrum for structures containing 1,2,4-trisubstituted benzene rings. The ratio between aromatic protons and aliphatic CH₂ protons calculated by integration of the signals is found to be 7/2. This proves that the SO₃H substituents are in the ortho-position to the uretdione group and that only one nucleus of the diisocyanate used as starting material has been sulphonated.

EXAMPLE 2

69.5 g (¼ mol) of 3,3'-dimethyl-4,4'-diisocyanatodiphenylmethane are reacted in 300 ml of 1,2-dichloroethane with 11 ml (approximately ¼ mol) of SO₃ by a procedure analogous to that described in Example 1. The uretdione derivative of the following formula:

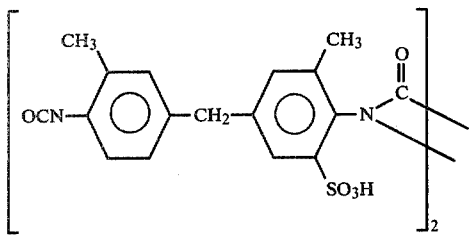

is obtained as a pink powder. Yield: 50% of the theoretical yield; m.p. > 280° C. with decomposition.

| Analysis: | C % | H % | N % | O % | S % |
|---|---|---|---|---|---|
| Calculated: | 57.0 | 3.9 | 7.8 | 22.3 | 9.0 |
| Observed: | 56.2 | 4.2 | 7.2 | 22.6 | 9.5 |

IR spectrum: 2280 cm⁻¹ (intense) NCO band; 1770 cm⁻¹ (intense) uretdione band; 1185 cm⁻¹ SO₃H band.

The position of the uretdione band at 1770 cm⁻¹ corresponds very accurately to the shift of the uretdione band by the orthosulphonic acid group discussed in Example 1. In the present case, this band shift is partly compensated by the ortho-methyl group which is also present.

NMR spectrum: Signals between 6.80 and 7.60 ppm: aromatic protons; Integration: 5 protons; Signal at 3.60 ppm: CH₂ group; Integration: 2 protons; Signal at 2.10 ppm: CH₃ group; Integration: 6 protons.

EXAMPLE 3

69.5 g (¼ mol) of 4,4'-diisocyanato-dimethyl-diphenyl methane dissolved in 300 ml of 1,2-dichloroethane are sulphonated with 14 ml (0.33 mol) of SO₃ by the method described in Example 1. The precipitated white powder obtained is the uretdione derivative of the following formula:

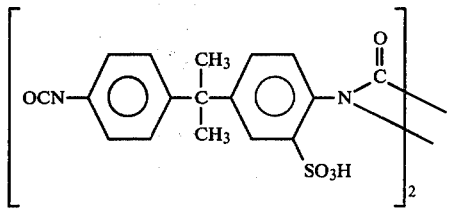

Yield: 33% of the theoretical yield; m.p. > 285° C. with decomposition. Evaporation of the solvent leaves a solid residue which consists of the diisocyanate used as starting material and uretdione derivative.

EXAMPLE 4

126 g (½ mol) of 4,4'-diisocyanato-diphenylether in 400 ml of 1,2-dichloroethane are reacted with 21 ml (½ mol) of SO₃ at 50° C. by the method indicated in Example 1. The partly precipitated pale yellow powder (m.p. > 280° C. with decomposition), as well as the residue obtained after evaporation of the dichloroethane consist predominantly of the uretdione derivative of the following formula:

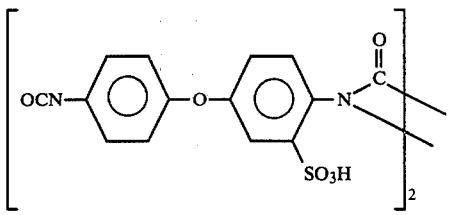

EXAMPLE 5

80 g (¼ mol) of 3,3'-dichloro-4,4'-diisocyanato-diphenylmethane in 300 ml of 1,2-dichloroethane are treated with 11 ml of freshly distilled SO₃ by the method described in Example 1, but at from 25° to 30°

C. After evaporation of the solvent, the desired uretdione derivative of the following formula:

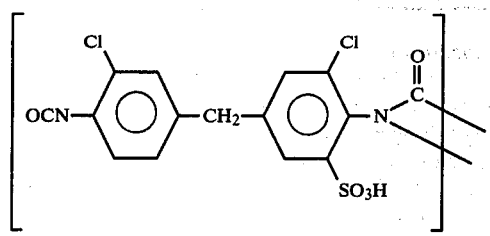

is obtained. Melting point > 280° C. with decomposition.

We claim:

1. Pulverulent crystalline aromatic uretdione diisocyanate disulphonic acids corresponding to the following formula:

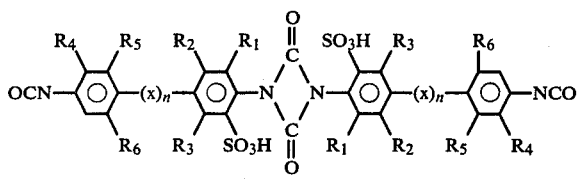

wherein

R$_1$, R$_2$, R$_3$, R$_4$, R$_5$ and R$_6$ each represent a hydrogen, chlorine or bromine atom or a methyl, ethyl or C$_1$–C$_4$ alkoxy group;

x represents —O—, >C=O, >SO$_2$, or

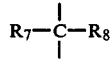

wherein R$_7$ and R$_8$ each represent a hydrogen atom, a methyl or ethyl group or, when taken together with the carbon atom to which they are attached represent a cyclohexyl group; and n represents 0 or 1.

2. A process for the preparation of pulverulent crystalline aromatic uretdione diisocyanate disulphonic acids, characterized in that a diisocyanate corresponding to the following general formula:

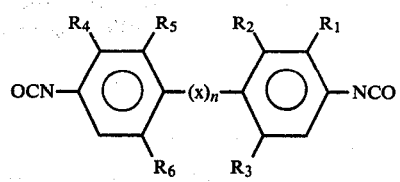

wherein

R$_1$, R$_2$, R$_3$, R$_4$, R$_5$ and R$_6$ each represent a hydrogen, chlorine or bromine atom or a methyl, ethyl or C$_1$–C$_4$ alkoxy group;

x represents —O—, >C=O, >SO$_2$, or

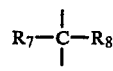

wherein R$_7$ and R$_8$ each represent a hydrogen atom, a methyl or ethyl group or, when taken together with the carbon atom to which they are attached represent a cyclohexyl group; and n represents 0 or 1, is reacted with sulphur trioxide at temperatures of from −30° to +100° C. in anhydrous solvents which are inert towards SO$_3$ and isocyanate groups.

3. The process of claim 2, wherein the reaction is carried out with gaseous SO$_3$ diluted with inert gas.

4. The process of claim 2, wherein the molar ratio of diisocyanate to sulphur trioxide is from about 1:1 to about 1:1.4.

5. The process of claim 3, wherein the inert gas/SO$_3$ mixture is passed over the surface of the reacting mixture while the reacting mixture is vigorously stirred.

6. The process of claim 2, wherein said sulphur trioxide is in the form of addition compounds with organic compounds which are capable of liberating sulphur trioxide.

7. The process of claim 2, wherein the reaction temperature is between about −10° and about +30° C.

8. The process of claim 2, wherein the reaction temperature is between about −5° to +10° C.

9. The process of claim 2, wherein said anhydrous solvent is 1,2-dichloroethane.

* * * * *